United States Patent [19]

Hawkins et al.

[11] Patent Number: 4,489,162

[45] Date of Patent: Dec. 18, 1984

[54] FRESH BLOOD (UNFIXED) HEMATOLOGY CONTROL

[75] Inventors: Pamela L. Hawkins; Carole J. Young, both of Miami, Fla.

[73] Assignee: American Hospital Supply Corporation, Evanston, Ill.

[21] Appl. No.: 332,781

[22] Filed: Dec. 21, 1981

[51] Int. Cl.³ .................... G01N 33/48; G01N 33/96; C09K 3/00

[52] U.S. Cl. ...................... 436/10; 424/101; 435/2; 436/15; 436/17; 436/18

[58] Field of Search ............... 436/10, 15, 17, 18; 435/2; 424/101

[56] References Cited

U.S. PATENT DOCUMENTS

| | | | |
|---|---|---|---|
| 3,873,467 | 3/1975 | Hunt | 436/10 |
| 3,973,913 | 8/1976 | Louderback | 436/18 |
| 4,027,971 | 6/1977 | Kolman et al. | 436/10 |
| 4,102,810 | 7/1978 | Armstrong | 436/10 |
| 4,213,876 | 7/1980 | Crews et al. | 436/10 |
| 4,224,313 | 9/1980 | Zimmermann et al. | 436/10 |
| 4,224,942 | 9/1980 | Wu et al. | 436/10 |
| 4,267,269 | 5/1981 | Grode et al. | 436/10 |
| 4,289,756 | 9/1981 | Zimmermann et al. | 436/17 |
| 4,299,726 | 11/1981 | Crews et al. | 436/10 |
| 4,356,172 | 10/1982 | Nakao et al. | 435/2 |

FOREIGN PATENT DOCUMENTS 152719  12/1981  German Democratic Rep. ... 436/10

*Primary Examiner*—Teddy S. Gron
*Attorney, Agent, or Firm*—John H. Faro

[57] ABSTRACT

Hematologic control and calibration standards are disclosed which are essentially plasma-free. These controls are prepared by the suspension of red blood cells in an appropriate buffer containing a stabilization effective amount of disaccharides, and other optional ingredients. Control and calibration standards prepared in the foregoing manner are suitable in the control and calibration of hematology analyzers for the following parameters: white cell count, red cell count, hemoglobin, hematocrit and the common derived parameters (i.e., mean cell volume, mean cell hemoglobin and mean cell hemoglobin concentration). The addition of platelets to the foregoing suspensions is also contemplated to provide a control for platelet parameters.

9 Claims, 5 Drawing Figures

FRESH BLOOD (UNFIXED) HEMATOLOGY CONTROL

Field Of The Invention—This invention is directed to a composition and to a method. More specifically, this invention concerns itself with hematologic control fluids which are substantially plasma-free, have properties comparable to fresh blood and a shelf life comparable to stabilized cells. This invention is also inclusive of hematologic fluids useful in the calibration of automated hematology analyzers.

Description Of The Prior Art—The use of control fluids is essential in assessing the accuracy and precision of results in the clinical hematology laboratory. Usually, commercial controls are comprised of stabilized blood suspensions which have been carefully assayed for the differing blood parameters. These parameters include the white blood count (WBC), red blood count (RBC), hemoglobin (Hb), hematocrit (Hct) and derived parameters such as mean cell volume (MCV), mean cell hemoglobin (MCH) and mean cell hemoglobin concentration (MCHC). When platelets are added to these controls, platelet parameters are also assayed. Clinical laboratories use commercial controls to assist them in assessing the accuracy and precision of their instruments and methods and, thus, the accuracy of patient blood sample parameters reported by such instruments.

Controls are not intended to be used in the calibration of hematology instruments. The generally recommended procedure for calibration of hematology analyzers usually requires the use of 10 to 20 fresh blood samples. Values for these samples are obtained by performing replicate determinations using accepted reference methods. The reference values obtained in this fashion are thereupon used to set or adjust the instrument so that valid results can be obtained on controls and on patient samples. By far, the most tedious, time consuming and error-prone part of the fresh blood calibration is the establishment of these reference values. A blood calibrator which has been carefully assayed and has stable, reliable parameter values can be used in place of fresh blood calibration, thus, helping to eliminate errors which are inherest in the fresh blood reference procedures. With the availability of such a calibrator, the function or accuracy of the instrument can be checked more frequently and with greater ease.

The various types of hematology cell controls can be divided into two separate and distinct groups. The first such group is comprised of a fresh cell preparation in a nutrient medium (which may contain glucose). Due to its relative instability, such fresh cell controls have abbreviated shelf life (approximately 30 days) and are often susceptable to mishandling both in shipment and in laboratory use. The second type of control material is characterized as a semi-fixed or stabilized cell preparation. "Stabilized" in this context contemplates the treatment given to the cell to increase their stability while at the same time preserving the cell's ability to undergo lysis.

While such stabilized cells are more resistant to mishandling in shipment and to misuse in the laboratory, such stabilization processes can alter, in an adverse fashion, some properties of the cell which are subject to such treatment. Frequently, cells which are subjected to such stabilization are more resistant to lysis than fresh cells and may behave differently than fresh cells. Moreover, such stabilized blood cells are generally more difficult to mix than fresh red cells making them difficult to use and thus affecting their function in instrument control.

The above stabilization processes also generally increase supernatant hemolysis to unacceptable levels, which interferes with the measuring processes of certain light sensing instruments. For example, in the TECHNICON Hemalog D, such hemolysis can distort the control's hematocrit measurement result which is determined by a light sensing means within that device. Similar adverse results are experienced in instruments which count and size cells using laser technology. Thus, such supernatant hemolysis, together with the increased resistance to lysis resulting from the stabilization process, make such stabilized cell controls less desirable for these particular types of instruments. Differences are also experienced when one compares fresh cells controls with stabilized cell controls in a COULTER Model S series instrument utilizing an azide-containing diluent in lieu of an azide-free diluent. The reference microhematocrit differs from the hematocrit obtained on instruments calibrated with fresh blood.

It is thus obvious from the foregoing discussion, that an improved control is required which would possess increased stability and yet preserve its behavior as a fresh cell both with regard to lysis and relative supernatant clarity. Ideally, such a control should also exhibit no azide vs. azide-free diluent bias. The above properties would also be highly desirable in a calibrator. In addition, it is essential that a calibrator perform as fresh blood when analyzed by reference methods. A critical parameter in this regard is the hematocrit. The microhematocrit should "match" hematocrits obtained on fresh blood calibrated instruments. Thus, if the control, with slight modification, could also be used as a calibrator, it would also offer substantial improvement to the systems currently available.

SUMMARY OF THE INVENTION

Accordingly, it is the principle object of this invention to remedy the above as well as related deficiencies in both fresh cells and stabilized cell controls used in the clinical hematology laboratory.

More specifically, it is the object of this invention to provide a hematology control fluid which possesses both the properties of fresh cells and yet the shelf life of a stabilized cell preparation.

It is yet another object of this invention to provide a hematology control fluid which possesses essentially the same tendency of fresh cells to undergo lysis and yet is essentially free of supernatant induced hemolysis.

It is still yet another object of this invention to provide a hematology control fluid which is also suitable in the calibration of hematology instruments.

The above and related objects are achieved by providing an essentially plasma-free fluid suspension comprising a pre-determined amount of washed red blood cells in a buffered medium, having a pH of about 6.8 to 8 and a stabilization effective amount of a disaccharide. The foregoing suspension provides a stable hematology control having an extended useful shelf life, is free from the problems associated with more traditional methods of stabilization and equivalent in performance to fresh blood. Such controls may be further modified through the addition of appropriate quantities of bovine serum albumin and polysaccharides, such as dextran, for use as calibrators of hematology instruments. The surprising and prolonged stability of the cells in this fluid suspension is believed to be attributable to the judicious and conscious control of the osmolality of the suspension so as to minimize ionic transport across the red blood cell (RBC) membrane and thus place the cells in an environment which attempts to preserve the native ionic concentration within the red blood cells. This maintenance of an osmotic equilibrium across the RBC membrane is achieved, in part, through minimization of sodium ion concentration in the buffer solution and through the relatively high concentration of disaccharide in the fluid suspension. The relatively large concentration of disaccharide and low osmolality medium (on the order of 240 to 310 mos/kg) helps insure maintenance of the cells in a resting state. Because sodium ion concentration in the buffer is believed to be a contributing factor to the cell instability, the use of a potassium buffer is generally preferred.

DESCRIPTION OF THE INVENTION INCLUDING PREFERRED EMBODIMENTS

Figure 1:
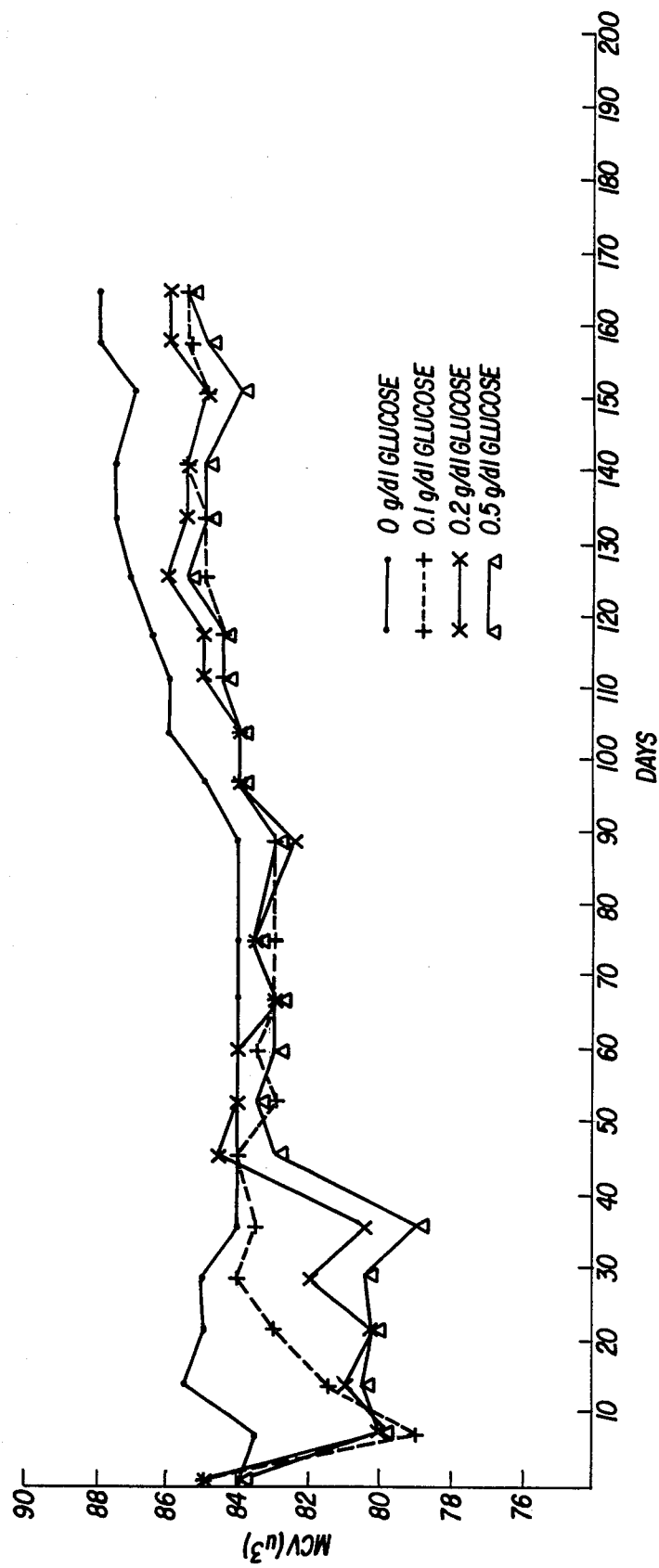
FIG. 1 graphically illustrates changes in mean cell volume of a fresh red blood cell suspension when varying concentrations of glucose are added to the suspension.

Both the hematology controls and calibrators contemplated within the scope of this invention can be readily prepared utilizing standard techniques and readily available materials. Either freshly drawn or outdated red blood cells may be used since the stabilizing medium of this invention is effective to prevent either from further deterioration. Employing standard cell washing techniques, the cells are washed with enough saline to remove essentially all plasma. Plasma removal is necessary since it contains antibodies which can react with antigens of different blood groups. Thereafter, the washed cells of different blood groups can be combined and the resulting mixture used in the preparation of the hematology controls and calibrator preparations of this invention. Subsequent to the washing of the cells with saline, the saline is removed by conventional methods, the cells are again washed and resuspended in a buffered medium. The components of the buffered medium can vary depending on whether or not the intent is to prepare simply a control or to prepare a calibrator. Fixed cells, to simulate white blood cells, and if desired, platelets, can also be added to the buffered medium containing the essentially plasma-free red blood cells. All of the foregoing steps in the formulation of the above hematology preparations are performed using aseptic techniques. Because there is less physical manipulation of the red blood cells in the above procedure than in conventional stabilized cell preparation, there is less likelihood of contamination. Once having prepared the control/calibrator suspension, the resultant preparation will undergo an equilibration period, during which time the mean cell volume and hematocrit values will stabilize. This stabilization can vary from a few days to several weeks, depending upon the various concentrations of components within the medium and whether or not any nutrient, such as glucose, is also present in the medium. Thus, the conscious addition of glucose is preferably minimized in the preparation of these controls and calibrators.

The hematology cell preparation suitable for use as controls requires a buffered environment and relatively high concentrations of disaccharide (on the order of 5 to 50 grams per liter of buffered medium). The buffer which is suitable for use in preparation of these controls may be a sodium or potassium phosphate buffer capable of maintaining the suspensions at a pH in the range of from about 6.8 to about 8. In one of the preferred embodiments of this invention, the sodium ion concentration of the preparation is minimized even further. A potassium phosphate buffered medium and various Good's buffers are among those suitable for use in this regard.

The concentration of various ingredients within the suspension is also carefully controlled in order to maintain its osmolality within the range of about 240 to 340 mos/kg. Thus, when the concentration of one component of the suspension is changed, there also must be a corresponding change in the relative concentrations of other components present therein in order to maintain the osmolality within the prescribed range for maximum cell stability.

The hematology control fluids suitable for use as controls can be further modified through the addition of certain ingredients and, thus, function as calibrators for hematology instruments. Two ingredients which can be added to the control fluid to impart calibrator properties are serum albumin (SA) and high molecular weight polysaccharides, such as dextran. The relative concentration of serum albumin in the control in the range from about 2 to 8 grams/deciliter have been found to impart calibration properties to the fluid. The relative concentration of polysaccharide (preferably having mean molecular weight of approximately 500,000 or greater) should be in the range of from above 0.1 to about 1.0 grams/dl.

Other optional ingredients which can be added to the medium to modify and/or alter its properties include such standard additives as adenine and inosine. These optional components can be added to the calibrator medium at the usual and customary relative concentrations for hematology fluids. As noted previously, the suspension should be maintained essentially free of nutrients, such as monosaccharides, insofar as the addition thereof to the suspension will result in a relatively extensive equilibration period before the resultant control/calibrator can be used in the clinical environment. In addition to the foregoing required and optional ingredients, such controls and calibrators can also contain other unspecified ingredients to the extent that such ingredients do not effect, in an adverse fashion, either the cell stability, the interaction of the essential components of the suspension with the red blood cells or the osmolality of the fluid suspension.

Subsequent to the preparation of the controls and calibrators in the matter described hereinabove, they are evaluated utilizing both manual and automated techniques in order to determine the relative stability of the preparation and reproducibility of results. In addition, the various preparations within the scope of this invention are also compared with one another in order to determine the optimal levels of the various components present therein.

EXAMPLES

The Examples which follow further define, describe and illustrate a number of the preferred embodiments of this invention including comparison thereof to the more traditionally available controls and calibrators. Parts and percentages appearing in such examples are by weight unless otherwise stipulated. Apparatus and techniques which are used in both the preparation of the following controls and calibrators are either performed manually or on commercially available automated equipment utilizing generally accepted and established practices.

EXAMPLE 1

Red blood cells are separate from a whole blood specimen by conventional techniques, washed with saline for removal of essentially all plasma and thereafter resuspended in a buffered medium. The cell concentration in such medium is in the range of $4-5 \times 10^6$ per cubic microliter. The other components of the medium are as follows:

| Sodium phosphate | 32 mM |
|---|---|
| KCl | 5 mM |
| Lactose | 30 g/l |
| BSA | 4 g/l |
| Chloramphenicol | 0.5 g/l |
| Neomycin sulfate | 0.3 g/l |
| Osmolality | 280 mos/kg |
| Glucose concentration varied | 0–0.5 g/dl |

The mean cell volume stability of 4 samples containing 100, 200 and 500 milligrams of glucose per deciliter are compared with a sample essentially devoid of any glucose. FIG. 1 illustrates the relative stability of these 4 preparations. As is readily apparent from review of the graphical data, the cell preparation, which is essentially deficient in glucose, does not require a prolonged equilibration period (on the order of 50 days) before it is stabilized sufficiently to have utility as a hematology control. In all the cell preparations depicted in FIG. 1, it is obvious that their relative stability deteriorates progressively with the passage of time.

EXAMPLE 2

The procedures of Example 1 repeated except for modification in composition of the control, which is as follows:

| Base | Potassium phosphate | 16 mM |
|---|---|---|
| | KCl | 96 mM |
| | NaCl | 8 mM |
| | MgCl | 2 mM |
| | Chloramphenicol | 0.5 g/l |
| | Osmolality | 280 mos/kg |

Concentration of:

| Lot | Glucose | BSA | Lactose |
|---|---|---|---|
| 3 | 0.5 g/dl | 4 g/dl | 3.45 g/l |
| 4 | 0.5 g/dl | 4 g/dl | 0 |
| 8 | 0 | 4 g/dl | 6.9 g/l |

-continued

| Lot | Glucose | BSA | Lactose |
|---|---|---|---|
| 12 | 0 | 0 | 20.7 g/l |

Figure 2:
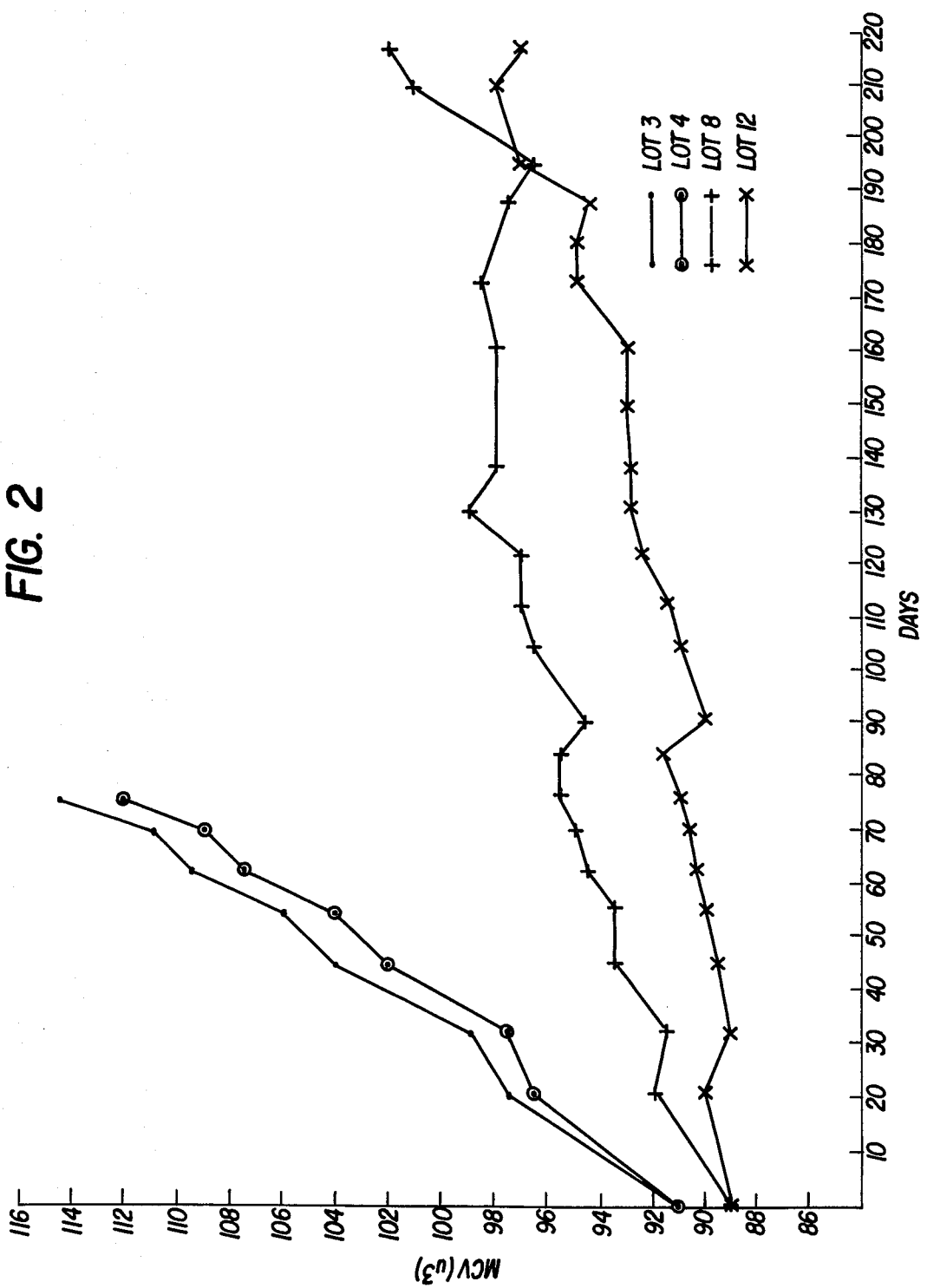
FIG. 2 graphically illustrates a comparison between a fresh cell preparation containing disaccharide and a preparation deficient in disaccharide.

As noted hereinabove, the samples which are prepared have differing concentrations of glucose, bovine serum albumin (BSA) and disaccharide (lactose). As is evident from the graphical depiction of mean cell stability in FIG. 2, the preparations containing the monosaccharide (glucose) are considerably less stable than the preparation containing the disaccharide (lactose).

EXAMPLE 3

The procedures of Example 1 are repeated except for modification in the composition of the control, which is as follows:

| Base | Sodium phosphate | 16 mM |
|---|---|---|
| | KCl | 5 mM |
| | Chloramphenicol | 0.5 g/l |
| | Osmolality at | 305 mos/kg |

Concentration of:

| Lot | Lactose | Glucose | BSA |
|---|---|---|---|
| 1 | 15 g/l | 5 g/l | 0 |
| 2 | 15 g/l | 0 | 4 g/dl |
| 3 | 0 | 0 | 4 g/dl |
| 4 | 0 | 5 g/l | 4 g/dl |
| 5 | 15 g/l | 5 g/l | 2 g/dl |
| 6 | 15 g/dl | 5 g/l | 4 g/dl |

Figure 3:
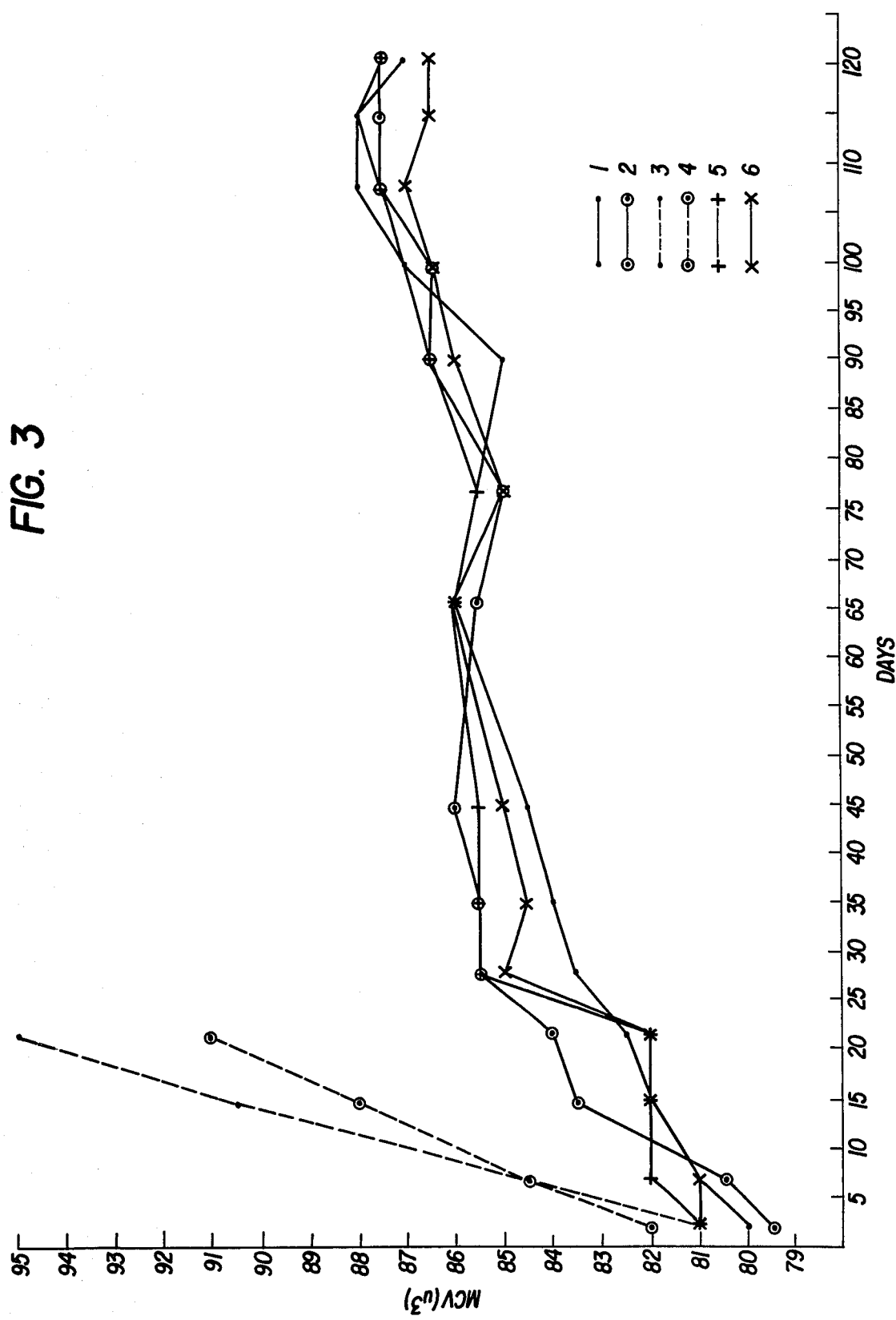
FIG. 3 graphically illustrates the comparative stability of fresh red blood cell suspensions containing various monosaccharides and various disaccharides.

The stability of these controls, as measured by variation in mean cell volume, is depicted for the 6 samples in FIG. 3. As is evident from the graphical illustration contained in FIG. 3, the preparations deficient in lactose are unstable when compared to the other preparations illustrated therein.

EXAMPLE 4

The procedure of Example 1 is repeated except for the modification in the composition of the control which is as follows:

| Sodium phosphate | 32 mM |
|---|---|
| KCl | 5 mM |
| BSA | 4 g/dl |
| Chloramphenicol | 0.5 g/l |
| Osmolality | 280 mos/kg |
| Various sugars | 87.7 mM |

Figure 4:
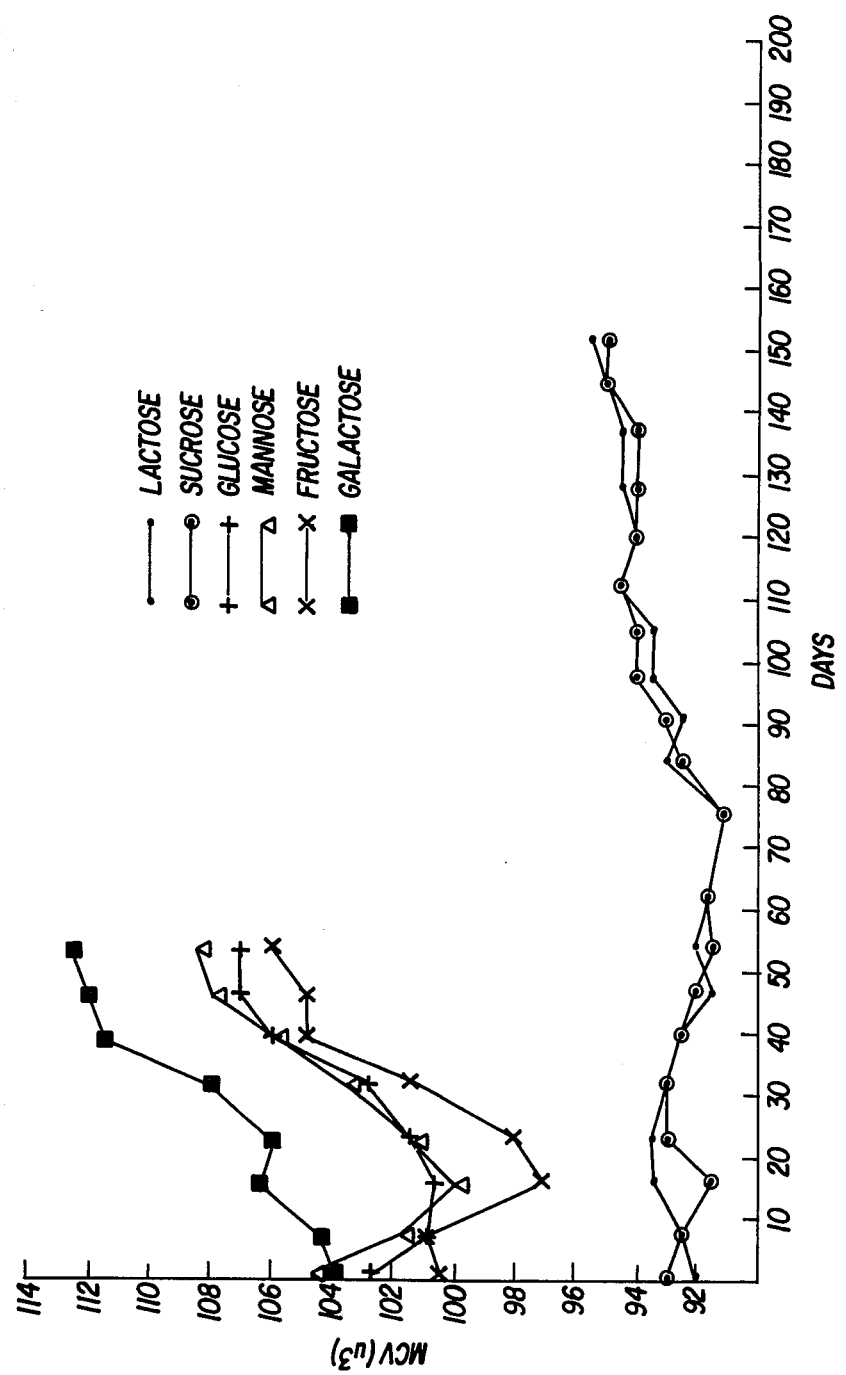
FIG. 4 graphically illustrates the comparative stability of fresh red blood cell suspensions containing various monosaccharides and various disaccharides.

From a comparison of the mean cell volume stabilities from the samples prepared with either a monosaccharide or a disaccharide, it is apparent from FIG. 4 that the preparations containing disaccharides exhibit essentially linear stability in comparison with those containing the monosaccharide. Of the two samples which exhibit good mean cell volume stability, there is essentially no difference between the sucrose containing preparation and the lactose containing preparation.

EXAMPLE 5

The procedure of Example 1 is repeated except for modification in the composition of the control preparation, which is as follows:

| | |
|---|---|
| Potassium phosphate | 32 mM |
| NaCl | 8 mM |
| Chloramphenicol | 0.5 g/l |
| Neomycin sulfate | 0.3 g/l |
| BSA | 4 g/dl |
| Inosine | 7.45 mM |
| Adenine | 2.95 mM |
| Dextran (500K) | 5 g/l |
| Osmolality | 260 mos/kg |
| Lactose | 20 g/l |

Figure 5:
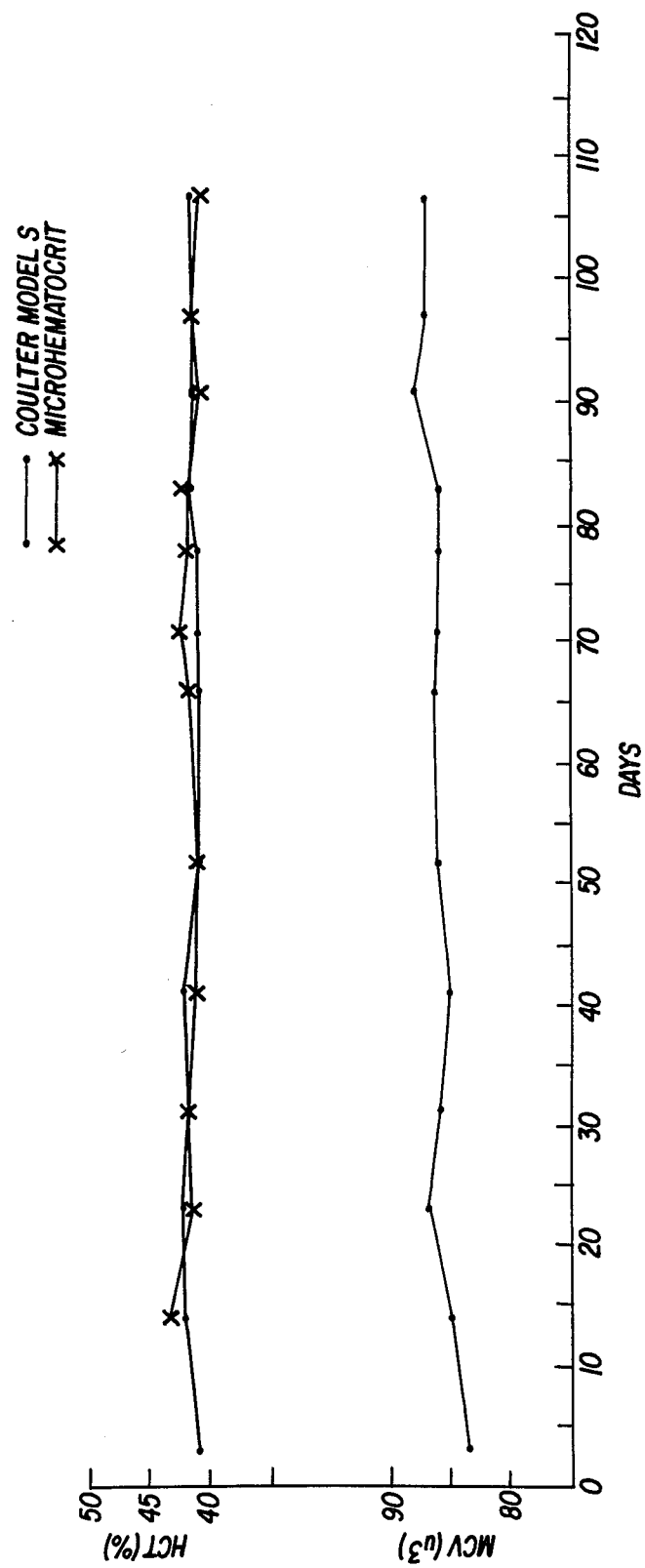
FIG. 5 graphically illustrates the essentially linear stability of certain of the preferred controls of this invention.

As evident from the graphical illustration in FIG. 5, three of the compositions prepared according to the foregoing recipe, the stability of the sample is essentially linear when measured as a function of mean cell volume or hematocrit.

The foregoing examples have been provided as illustrative of some of the preferred embodiments mentioned herein and are not intended as a delineation of its scope which is set forth in the claims which follow.

What is claimed is:

1. A fluid comprising an essentially plasma and nutrient free hematologic control and calibration standard having a predetermined amount of washed and unfixed red blood cells in a low sodium buffered medium, a pH range of about 6.8 to about 8 and a stabilizer consisting essentially of about 5 to about 50 grams of a disaccharide per liter of buffered medium, the concentration of disaccharide and sodium ions relative to other unspecified components of the fluid being adjusted so as to (i) maintain the osmolality of the fluid in the range of from about 240 to about 310 mos/kg and (ii) preserve the native ionic concentration within the red blood cells, whereby an osmotic equilibrium across the red blood cell membrane is achieved thereby minimizing ionic transport across the red blood cell membrane.

2. The essentially plasma-free fluid suspension of claim 1, wherein the disaccharide is selected from the group consisting of lactose, sucrose, maltose and mixtures thereof.

3. An essentially plasma-free fluid suspension of claim 1, wherein the concentration of disaccharide is in the range of about 15 mM to about 145 mM.

4. The essentially plasma-free fluid suspension of claim 1, wherein the osmolality of the suspension is maintained within the range of from about 260 to about 300 mos/kg.

5. The essentially plasma-free fluid suspension of claim 1, containing serum albumin at a concentration in the range of about 2 to 8 grams/dl suspension.

6. The essentially plasma-free suspension of claim 1, containing a polysaccharide having a mean molecular weight in excess of 500,000 and being present in the suspension of the concentration in the range of from about 0.1 to about 1 gram/dl.

7. The essentially plasma-free fluid suspension of claim 6, wherein the polysaccharide is dextran.

8. The essentially plasma-free fluid suspension of claim 1, wherein the pH of suspension is in the range of from about 7.4 to about 7.5.

9. A fluid comprising a plasma and nutrient-free hematologic control and calibration standard having a predetermined amount of washed and unfixed red blood cells in a low sodium buffered medium, a pH range of about 6.8 to about 8.0 and a stabilizer consisting essentially of about 5 about 50 grams of a disaccharide per liter of buffered medium, the concentration of disaccharide and sodium ions relative to other unspecified components of this fluid being adjusted so as to (i) maintain the osmolality of the fluid in a range of from about 240 to about 340 mos/kg and (ii) to preserve the native ionic concentration within the red blood cells, thereby an osmotic equilibrium across the red blood cell membrane is achieved whereby minimizing an ionic transport across the red blood cell membrane, the pH of the fluid being maintained with the above range by a buffer selected from a group consisting of potassium phosphate and Good's buffers.

* * * * *